US008329190B2

(12) United States Patent
Vidal et al.

(10) Patent No.: US 8,329,190 B2
(45) Date of Patent: Dec. 11, 2012

(54) LIPOTEICHOIC ACID FROM LACTIC ACID BACTERIA AND ITS USE TO MODULATE IMMUNE RESPONSES MEDIATED BY GRAM-NEGATIVE BACTERIA, POTENTIAL PATHOGENIC GRAM-POSITIVE BACTERIA

(75) Inventors: Karine Vidal, Lausanne (CH); Anne Donnet-Hughes, Saint-Legier (CH); Dominique-Anne Granato, Grandvaux (CH); Irene Corthesy-Theulaz, Epalinges (CH)

(73) Assignees: Societe des Produits Nestle S.A., Vevey (CH); Nestec S.A., Vevey (CH)

( * ) Notice: Subject to any disclaimer, the term of this patent is extended or adjusted under 35 U.S.C. 154(b) by 591 days.

(21) Appl. No.: 12/246,991

(22) Filed: Oct. 7, 2008

(65) Prior Publication Data

US 2009/0142375 A1 Jun. 4, 2009

Related U.S. Application Data

(62) Division of application No. 10/478,079, filed as application No. PCT/EP02/04436 on Apr. 23, 2002.

(30) Foreign Application Priority Data

May 23, 2001 (EP) .................................... 01201958

(51) Int. Cl.
*A61K 39/00* (2006.01)
*A61K 39/385* (2006.01)
*A61K 45/00* (2006.01)
*A61K 47/00* (2006.01)

(52) U.S. Cl. .............. 424/197.11; 424/184.1; 424/185.1; 424/193.1; 424/234.1; 424/282.1; 424/439; 424/441; 424/442; 424/451; 424/457; 424/464; 424/491; 435/822; 435/853; 435/856; 435/857; 435/885

(58) Field of Classification Search ........................ None
See application file for complete search history.

(56) References Cited

U.S. PATENT DOCUMENTS

| | | | |
|---|---|---|---|
| 4,678,773 A | 7/1987 | Usami et al. | |
| 5,578,302 A | 11/1996 | Brassart et al. | |
| 5,998,482 A * | 12/1999 | David et al. | 514/626 |
| 6,180,100 B1 | 1/2001 | Bruce et al. | |

FOREIGN PATENT DOCUMENTS

| | | |
|---|---|---|
| EP | 0135820 | 4/1985 |
| EP | 0343544 | 11/1989 |
| JP | 09-238647 | 9/1997 |
| JP | 10-057031 | 3/1998 |
| JP | 10-191916 | 7/1998 |
| JP | 2001-000143 | 1/2001 |
| WO | WO 9420115 | 9/1994 |
| WO | WO 0148476 | 7/2001 |

OTHER PUBLICATIONS

Labeta, M., et al., "Innate Recognition of Bacteria in Human Milk is Mediated by a Milk-derived Highly Expressed Pattern Recognition Receptor, Soluble CD14," J. Exp. Med. (2000), vol. 191, pp. 1807-1812.
L. Mata, et al., "Intestinal colonization of breast-fed children in a rural area of low socioeconomic level," (1971) Ann New York Acad Sci, vol. 176, pp. 93-108.
Brassart, D. et al., "The use of probiotics to reinforce mucosal defense mechanisms," Trends Food Sci Technol, vol. 9, pp. 321-326, Oct. 1997.
Suda, Y., et al.,"Cytokine-inducing glycolipids in the lipoteichoic acid fraction from *Enterococcus hirae* ATCC 9790," FEMS Immunol Med Microbiol, vol. 12, pp. 97-112 (1995).
Arakaki, R., et al., "A lipoteichoic acid fraction of *Enterococcus hirae* activates cultured human monocytic cells via a CD14-independent pathway to promote cytokine production, and the activity is inhibited by serum components," FEMS Immunol Med Microbiol, vol. 22, pp. 283-291 (1998).
Dziarski, R., et al., "Interactions of CD14 with Components of Gram-Positive Bacteria," Chem. Immunol., (2000), vol. 74, pp. 83-107.

* cited by examiner

*Primary Examiner* — Debbie K Ware
(74) *Attorney, Agent, or Firm* — K&L Gates LLP

(57) ABSTRACT

The invention relates to a composition for modulating the immune responses induced by Gram negative bacteria, potential pathogenic Gram positive bacteria and/or their derivatives, comprising lipoteichoic acid from lactic acid bacteria as an active ingredient. It also relates to the use of a lipoteichoic acid from lactic acid bacteria as an active ingredient and/or lactic acid bacteria producing it and/or its supernatant of culture, in the manufacture of a medicament, an oral or topical product for cosmetic, dermatological or ophtalmological applications, a food or petfood composition for modulating bacterial colonization, immune responses and decreasing the inflammatory processes associated with bacterially-mediated disease and infection in the gastrointestinal tract, bone, skin, eye, ear, lung and oral cavity. The invention also relates to lipoteichoic acid selected thereof.

24 Claims, 7 Drawing Sheets

FIGURE 1
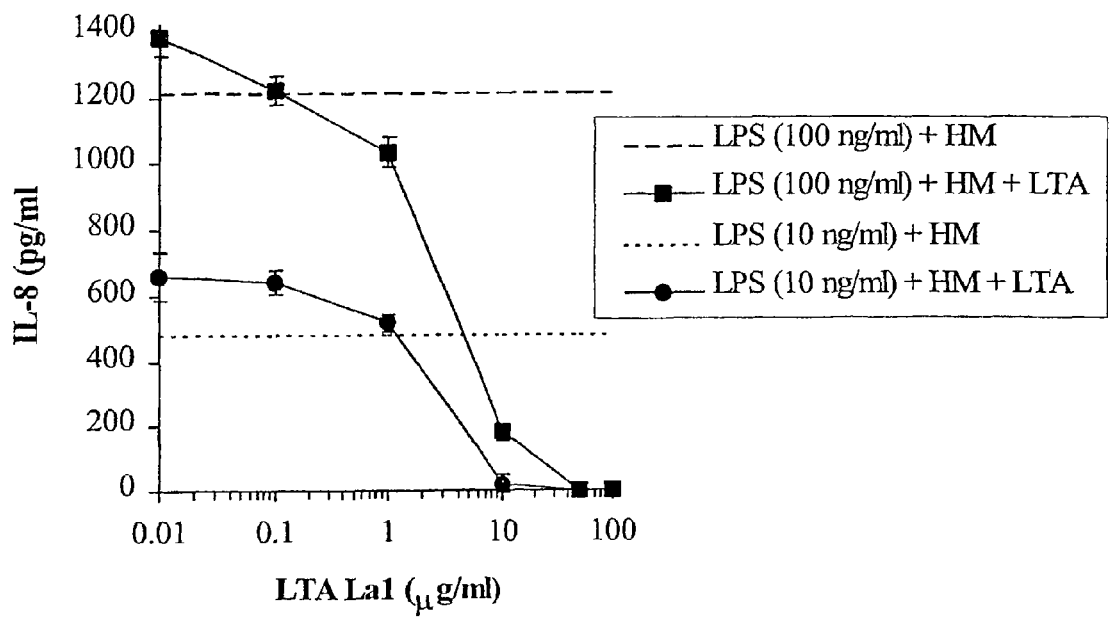
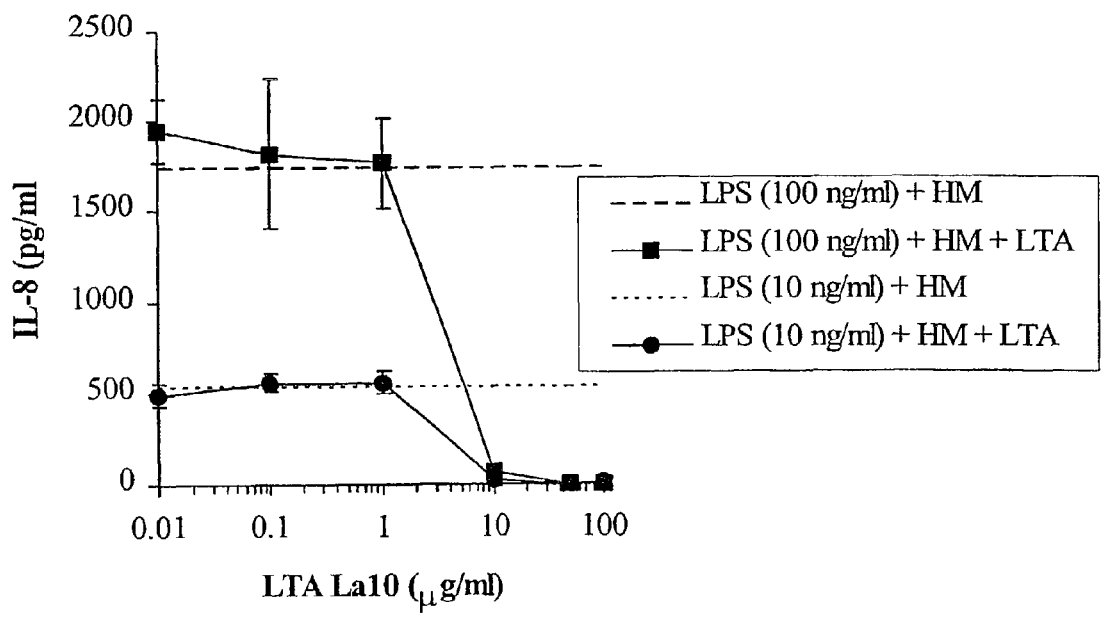

FIGURE 2   A
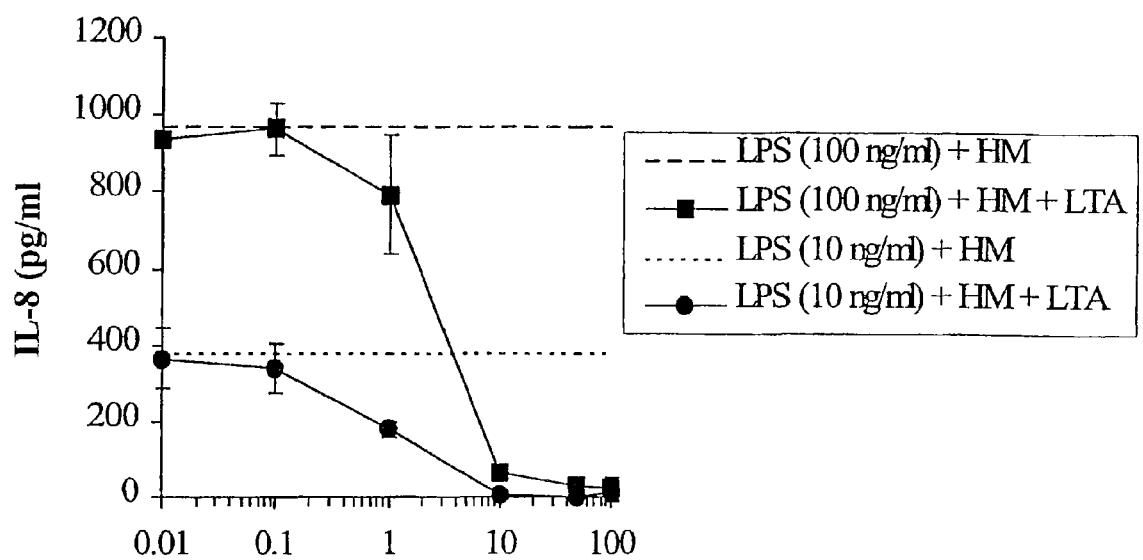
B
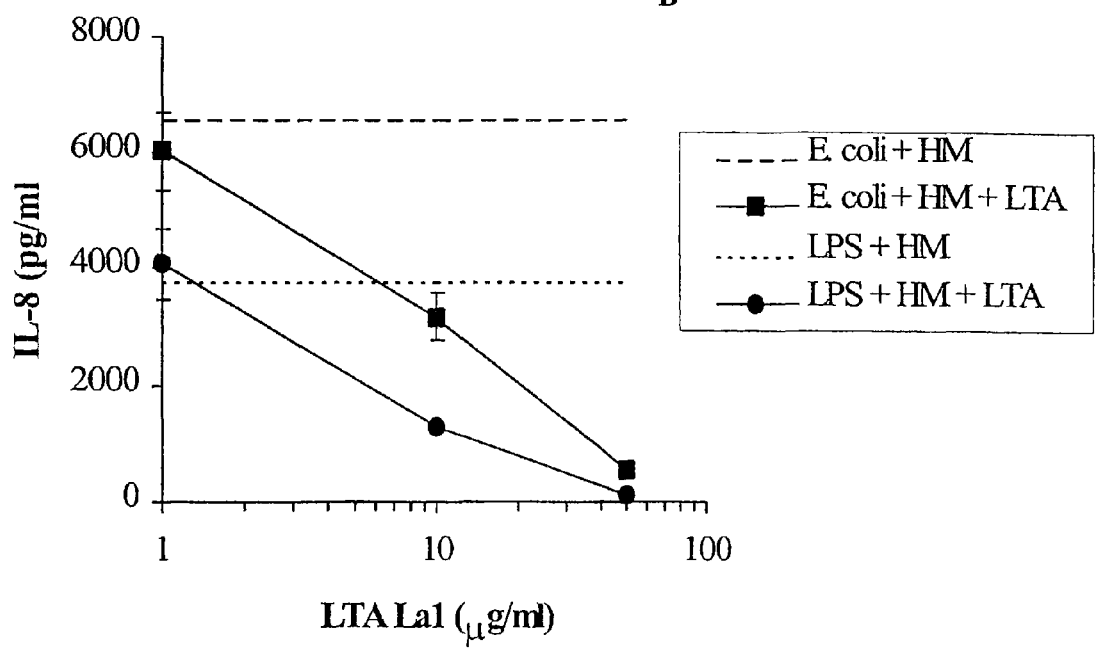

FIGURE 7
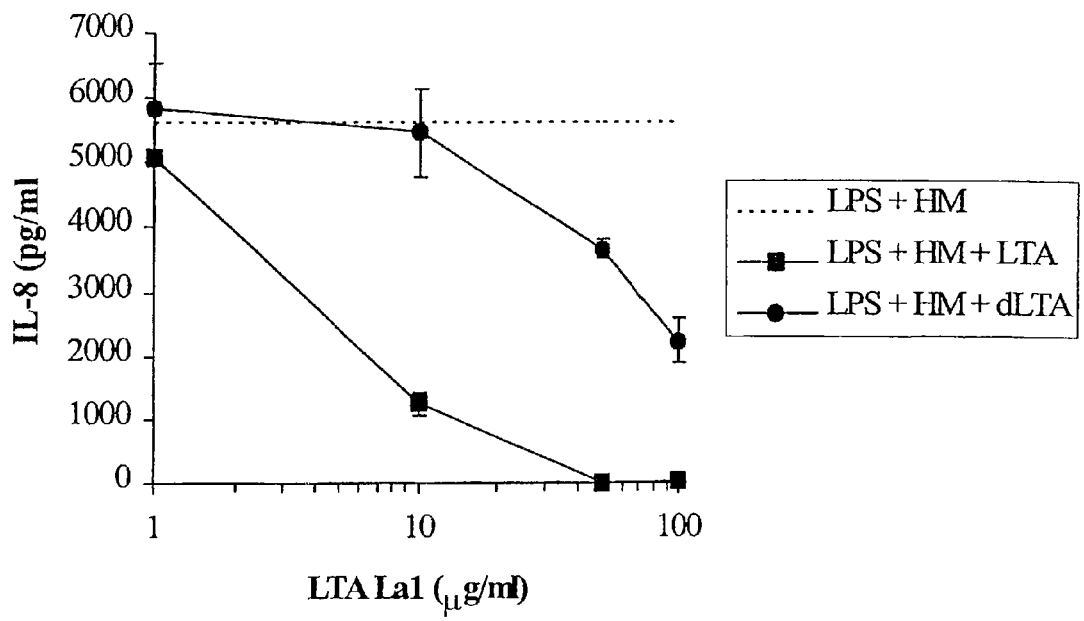
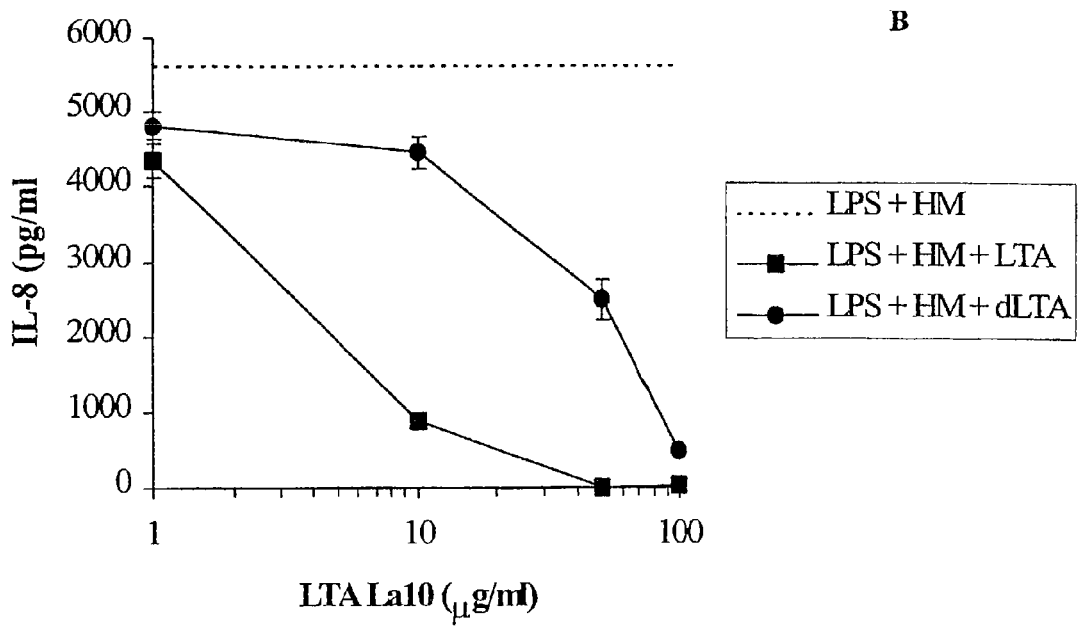

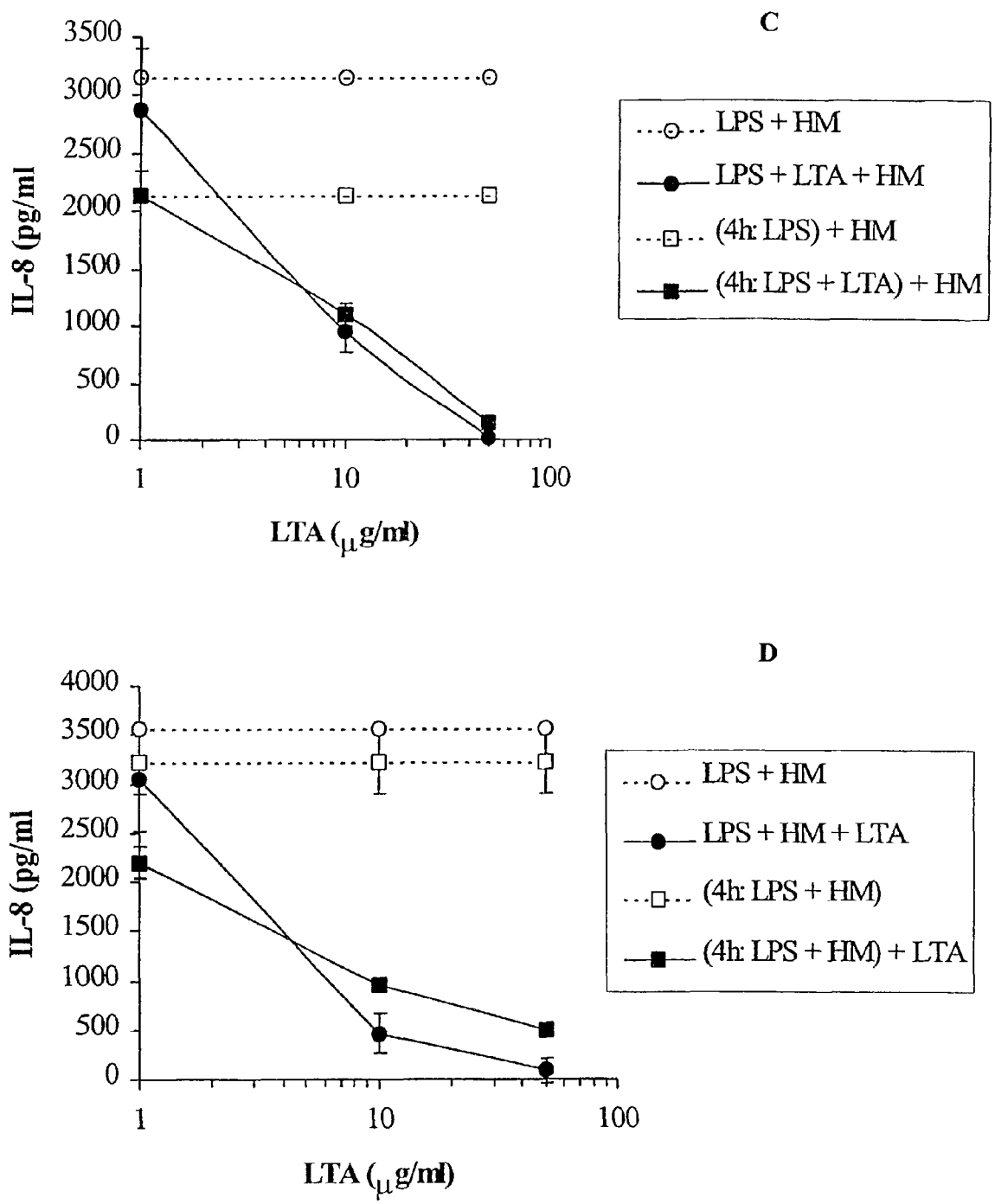

```
                         SEQUENCE LISTING

<160> NUMBER OF SEQ ID NOS: 2

<210> SEQ ID NO 1
<211> LENGTH: 17
<212> TYPE: DNA
<213> ORGANISM: artificial
<220> FEATURE:
<223> OTHER INFORMATION: ENA-78, 3' Antisense primer

<400> SEQUENCE: 1
cgttctcagg gaggctc                                                  17

<210> SEQ ID NO 2
<211> LENGTH: 18
<212> TYPE: DNA
<213> ORGANISM: artificial
<220> FEATURE:
<223> OTHER INFORMATION: ENA-78, 5' Sense primer

<400> SEQUENCE: 2
tccttcgagc tccttgtg                                                 18
```

LIPOTEICHOIC ACID FROM LACTIC ACID BACTERIA AND ITS USE TO MODULATE IMMUNE RESPONSES MEDIATED BY GRAM-NEGATIVE BACTERIA, POTENTIAL PATHOGENIC GRAM-POSITIVE BACTERIA

CROSS-REFERENCE TO RELATED APPLICATIONS

This application is a divisional of patent application Ser. No. 10/478,079, filed Nov. 18, 2003, which is the U.S. national stage designation of International application no. PCT/EP02/04436 filed Apr. 23, 2002, the entire content of which is expressly incorporated herein by reference.

FIELD OF THE INVENTION

The present invention relates to a composition containing lipoteichoic acid from lactic acid bacteria for modulating the immune responses induced by Gram negative bacteria, potential pathogenic Gram positive bacteria and/or their derivatives. It also relates to the use of a lipoteichoic acid from lactic acid bacteria as an active ingredient in the manufacture of a medicament, an oral or topical product for cosmetic, dermatological or opthalmological applications, a food or petfood composition for modulating bacterial colonisation, immune responses and decreasing the inflammatory processes associated with bacterially-mediated disease and infection in the gastrointestinal tract, bone, skin, eye, ear, lung and oral cavity. The invention also relates to lipoteichoic acid selected thereof.

BACKGROUND OF THE INVENTION

At parturition, there is colonisation of the previously sterile foetal intestine by a vast microbial inoculum. The establishment of the intestinal microflora is a very dynamic process during the first days of life before stable populations are established in defined regions of the gastrointestinal tract. There is sequential colonisation by first *E. coli* and Streptococci species (Mata, L. J. and J. J. Urrutia. 1971. *Ann NY Acad Sci* 176:93-108) and then a bifidogenic microflora, which is highly dominant in breast-fed babies and offers some protection against potential pathogens (Gibson, G. R. and X. Wang. 1994. *J Appl Bacteriol.* 77:412-420).

Lactic acid bacteria (LAB) such as lactobacilli and bifidobacteria are normal inhabitants of the human adult gastrointestinal tract. Selected strains from these genus, termed probiotics, have health benefits when administered orally to the host (Brassart, D. and E. J. Schiffrin. 1997. *Trends Food Sci Technol* 9:321-326). Like commensal LAB, probiotics antagonise pathogenic organisms and stimulate immune defence mechanisms. Although, little is known about the precise mechanisms which underlie these biological effects, it is widely accepted that strains which most likely exert health benefits are those which can transiently adhere to the intestinal epithelium, perhaps through the lipoteichoic acid (LTA) in their cell wall.

LTA is a complex glycero-phosphate polymer linked to a hydrophobic lipid moiety (Fischer, W. 1990. Bacterial phophoglycolipids and lipoteichoic acids. In Glycolipids, phosphoglycolipids and sulfoglycolipids, M. Kates, editor. Hanahan, D. J., New York and London. 123-234). It is a component of the cell wall of most Gram-positive bacteria and although there is great diversity in the LTA from different bacteria, it has structural similarities to LPS found in the cell wall of Gram-negative organisms.

While LPS from Gram-negative organisms are renowned for their pro-inflammatory effects on immune cells, less work has been done using LTA from Gram-positive organisms. It appears nevertheless that only LTA from specific species of bacteria mediate such effects (Suda, Y., et al. 1995, *FEMS Immunol Med Microbiol* 12:97-112; Arakaki, R., et al. 1998, *FEMS Immunol Med. Microbiol* 22:283-291)

Although LTAs from Gram-positive bacteria show great diversity from one bacterial strain to another, there is some structural similarity to the LPS present in the cell wall of Gram-negative organisms. Pattern Recognition Receptors (PRR) recognise conserved regions of bacterial structures and signal to the host the presence of a bacterial inoculum. CD14, a glycosylphosphatidyl-inositol (GPI)-anchored glycoprotein present on myeloid cells, is one such receptor. It is now known that it can bind both LTA and LPS. Indeed, the sepsis caused by Gram-negative organisms is through LPS binding to CD14 on the membrane of monocytes-macrophages. There is increasing evidence that a soluble form of the CD14 receptor mediates binding of LPS to CD14-negative cells. However, this molecule also recognises other bacterial components, such as peptidoglycan, lipoarabinomannan and manuronic acid polymers (Dziarski, R., et al., 2000. *Chem. Immunol.* 74:83-107). We have reported that a soluble form of CD14 (sCD14) present in human breast milk stimulates human intestinal epithelial cells (IECs) to release cytokines after challenge with non-pathogenic *E. coli* or its LPS (Labeta, M. O., et al. 2000. *J Exp Med* 191:1807-1812) but not after challenge with live Gram-positive bacteria or their cell wall components.

The present invention aims to provide a composition able to modulate the immune responses involved during bacterial colonisation or infection and prevent or reduce any inflammatory response induced thereby, in the gastrointestinal tract, bone, skin, eye, lung, ear and oral cavity in humans or animals.

SUMMARY OF THE INVENTION

Accordingly, in a first aspect, the invention provides a composition containing lipoteichoic acid from lactic acid bacteria as an active ingredient for modulating the immune responses induced by Gram negative bacteria, potential pathogenic Gram positive bacteria and/or their derivatives.

This composition containing lipoteichoic acid from lactic acid bacteria can maintain immune homeostasis, prevent or decrease inflammatory processes induced by Gram negative bacteria and/or for LPS-mediated disorders. It may also be use against pathogenic or potential pathogenic Gram positive bacteria and/or LTA-mediated disorders.

In fact, it has been found that there is an antagonistic effect of LTA from lactic acid bacteria strains, such as *Lactobacillus johnsonii* strain La1 and *Lactobacillus acidophilus* strain La10, for example, on the responsiveness of IECs challenged with LPS purified from *E. coli* and *Salmonella enteridis* or with whole *E. coli* bacteria. Also, when LTA from either of the Lactobacilli strains was given at the same time as LPS in the presence of human milk, the LPS-sCD14-mediated production of IL-8 was inhibited.

The said composition can be a medicament, an oral or topical cosmetic, dermatological or opthalmological product, a food or a pet food composition. It has effects on inflammatory process associated with bacterially-mediated disease or LPS-mediated disorders in the gastrointestinal tract, bone, skin, eye, lung, ear and oral cavity and can be used to modulate bacterial colonisation in the aforesaid tissues and the immune responses.

In another aspect the invention provides lipoteichoic acid from lactic acid bacteria that have been selected for their ability to bind to CD14 and for their inability to induce the release of proinflammatory cytokines such as IL-8 or TNF-α from IECs.

Given orally, lipoteichoic acid according to the invention can be used to maintain immune homeostasis, modulate bacterial colonisation, or target bacterially-mediated disease and infection or LTA/LPS-mediated disease not only in the gastrointestinal tract but also in bone, the skin, eye, ear, lung and the oral cavity.

Accordingly, in a further aspect the invention provides the use of at least one lipoteichoic acid from lactic acid bacteria for the preparation of a composition intended for modulating the immune responses induced by Gram negative bacteria and/or their derivatives. The lipoteichoic acid may be used in the manufacture of a medicament, a topical product such as a cream or a lotion, a food or pet food composition for decreasing inflammatory process associated with bacterially-mediated disease or LTA/LPS-mediated disorders in humans or animals.

In another aspect the invention provides a method of modulating the aforementioned responses in humans or animals, which comprises administering an effective amount of lipoteichoic acid from lactic acid bacteria or a composition containing it.

In a further aspect, the invention provides a method of modulating an immune response induced in a pet animal by Gram negative bacteria, potential pathogenic Gram positive bacteria and/or their derivatives, the method including administering a pet animal a composition containing a moiety of a probiotic bacterial strain capable of modulating such response.

It may include administering a pet animal a composition containing a probiotic micro-organism, its culture supernatant or a metabolite thereof, the said probiotic being capable of at least transiently adhering to the intestinal epithelium of the pet animal.

In an embodiment, the method includes administering the composition as a component of a nutritionally balanced meal. In a preferred embodiment, the component is included in a wet or dry pet food formulation.

In a last aspect, the invention relates to a pet food formulation comprising a nutritionally balanced meal and an active ingredient selected for its capacity to modulate an immune response induced in a pet animal by la Gram negative bacterial strain, potential pathogenic Gram positive bacterial strain and/or a derivative thereof.

In an embodiment, the active ingredient comprises a micro-organism having LTA. The LTA is preferably present in a cell wall of the said micro-organism.

The micro-organism is preferably a probiotic capable of transiently adhering to the intestinal epithelium of a pet ingesting it. In a preferred embodiment, the micro-organism is a lactic acid bacterium.

An advantage of the present invention is that it provides a means of regulating immune responses to Gram-negative organisms, pathogenic or potential pathogenic Gram-positive organisms or of their derivates LPS or LTA, in particular a means of decreasing inflammatory processes such as the production of proinflammatory cytokines such as IL-8, TNF-α and epithelial cell-derived neutrophil-activating protein (ENA)-78 by IECs.

Another advantage of the present invention is that it provides a means to down-regulate the inflammatory response of macrophages by, for example, decreasing the release of proinflammatory cytokines such as IL-8 and TNF-α.

Yet another advantage of the present invention is that by simple consumption of a food composition according to the present invention, the protective immune process in a mammal may be improved and the risk of deleterious inflammation and infection reduced. It will be appreciated that intravenous or subcutaneous administration of a drug requires expertise, and compared to oral administration it is not as safe, convenient or acceptable to the patient. In the light of these concerns, the invention provides the clear advantage of a nutritional and/or a therapeutic product which may be administered orally.

Furthermore, the present invention uses LTA from food-grade bacterial species and as such have GRAS (Generally Regarded As Safe) status and provides some of the benefits attributed to probiotic organisms. As such, the present invention can be used in sterile medicaments, enteral or topical compositions for clinical disorders and infections in which the use of living probiotic organisms is not possible.

BRIEF DESCRIPTION OF THE FIGURES

FIG. 1A shows the effect of LTA from *L. johnsonii* strain La1 on the release of IL-8 by HT29 cells challenged with LPS purified from *E. coli*.

FIG. 1B shows the effect of LTA from *L. acidophilus* strain La10 on the release of IL-8 by HT29 cells challenged with LPS purified from *E. coli*.

FIG. 2A shows the effect of LTA from *lactobacilli* La1 on the release of IL-8 by HT29 cells challenged with LPS from *Sal. enteridis*.

FIG. 2B shows the effect of LTA from *lactobacilli* La1 on the release of IL-8 by HT29 cells challenged with LPS from whole *E. coli* bacteria.

FIG. 7A shows the effect of deacylation of the LTAs on their antagonistic activity. HT29 cells were challenged with *E. coli* LPS (100 ng/ml) in medium supplemented with 2% human milk (HM) in the absence (dashed lines) or the presence (solid lines) of varying amounts of native LTA or deacylated LTA purified from La1. After 24 hours, the release of IL-8 in the culture supernatants was measured by ELISA.

FIG. 7B shows the effect of deacylation of the LTAs on their antagonistic activity. HT29 cells were challenged with E. coli LPS (100 ng/ml) in medium supplemented with 2% human milk (HM) in the absence (dashed lines) or the presence (solid lines) of varying amounts of native LTA or deacylated LTA purified from La10. After 24 hours, the release of IL-8 in the culture supernatants was measured by ELISA.

DETAILED DESCRIPTION

Figure 3:
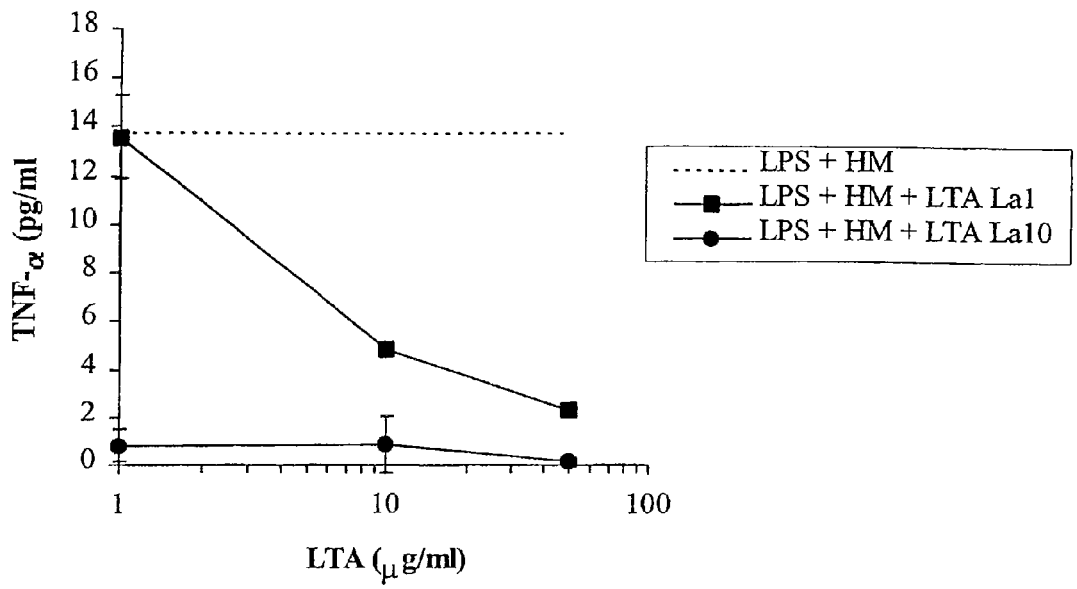
FIG. 3 shows the effect of LTA from the *lactobacilli* La1 and La10 on the release of TNF-α by HT29 cells challenged with *E. coli* LPS.

Within the following description, the following abbreviations have been used: ENA-78, epithelial cell-derived neutrophil-activating protein-78; HM, human milk; IECs, intestinal epithelial cells; IL, interleukin; LPS, lipopolysaccharide; LTA, lipoteichoic acid; mAb, monoclonal antibody; PBMC, peripheral blood mononuclear cells; PRR, pattern recognition receptors; TNF, tumour necrosis factor.

Finally, "NCC" designates Nestlé Culture Collection (Nestlé Research Centre, Vers-chez-les-Blanc, Lausanne, Switzerland).

According to a first aspect, a composition containing lipoteichoic acid from lactic acid bacteria for modulating immune responses, in particular inflammatory processes induced by Gram-negative bacteria, potential pathogenic Gram-positive bacteria and/or their derivatives, is concerned.

Such inflammatory processes may be induced by Gram-negative bacteria and/or its LPS of Gram negative bacteria, such as *Escherichia* ssp., *Helicobacter* spp, *Salmonella* spp, for example; they may also be induced by pathogenic or potential pathogenic Gram-positive bacteria, i.e. bacteria that may become pathogenic in certain conditions.

Preferably, the lipoteichoic acid from lactic acid bacteria has been selected for its ability to bind to CD14 and for its inability to induce the release of proinflammatory cytokines such as IL-8 or TNF-α from IECs. The lipoteichoic acid should contain its lipid moeity.

Preferably, lipoteichoic acid is isolated from bacteria belonging to the genus *Lactobacillus*, *Bifidobacterium* or *Streptococcus* such as the species *Lactobacillus acidophilus*, *Lactobacillus gasseri*, *Lactobacillus johnsonii*, *Lactobacillus helveticus*, *Lactobacillus casei*, *Lactobacillus plantarum*, *Bifidobacterium bifidum*, *Bifidobacterium longum*, *Bifidobacterium infantis*, *Bifidobacterium animalis*, *Streptococcus thermophilus*, for example; and most preferably *Lactobacillus johnsonii* strain La1 (NCC 533), *Lactobacillus acidophilus* strain La10 (NCC90), and *Lactobacillus gasseri* (NCC2493).

The strains *Lactobacillus johnsonii* NCC 533, *Lactobacillus acidophilus* NCC 90 have been deposited by way of example at the Institut Pasteur, 28 rue du Docteur Roux, F-75024 Paris cedex 15, FRANCE, on 30 Jun. 1992 and 12 Oct. 1999 respectively, under the deposit numbers CNCM I-1225 and CNCM I-2332, respectively.

In a most preferred embodiment, LTA from lactic acid bacteria may be used in combination with molecules such as sCD14.

Lipoteichoic acid and/or lactic acid bacteria producing it and/or its supernatant of culture may be incorporated into dry or liquid food compositions or enteral feeds, for infant nutrition, pet nutrition and animal feeds, for clinical nutrition or for pharmaceutical applications.

It can also be used for cosmetic or dermatological applications in the form of topical (creams and ointments) or oral preparations, ophthalmic applications (eyes washes), or oral applications (mouth washes, tooth pastes). LTA could be used to prevent ear infections. Furthermore, LTA in products can be used to prevent LPS-mediated bone disorders.

Accordingly, the said composition can be a medicament, an oral or topical cosmetic, dermatological or opthalmological preparation, a food or a pet food composition.

The amount of lipoteichoic acid to be used may vary but will correspond to levels of bacteria in a food composition which may vary from $10^5$ cfu/g to about $10^{11}$ cfu/g, most preferably from approximately $10^7$ cfu/g to $10^9$ cfu/g. In the case of pharmaceutical preparation, the amount of LTA may vary and correspond to an amount of bacteria which varies from $10^5$ cfu/g to $10^{16}$ cfu/g, preferably from approximately $10^7$ cfu/g to $10^{10}$ cfu/g.

It has effects on inflammatory process associated with bacterially-mediated disease or LTA/LPS-mediated disorders in the gastrointestinal tract, bone, skin, eye, ear, lung and oral cavity.

More specifically, these products could modify bacterial colonisation and infection during the neonatal period, and thereby the immune competence of the infant, and in clinical nutrition, be used to treat sepsis, bacterial translocation, inflammation, infection and disease, and bacterial overgrowth.

In a preferred embodiment, the composition may be a complete and nutritionally balanced food or pet food. It can also be a dietary supplement, for example.

If a food composition for human consumption is prepared, it may be a nutritionally complete formula, a dairy product, a chilled or shelf stable beverage, a soup, a dietary supplement, a meal replacement, a nutritional bar or a confectionery.

Apart from the lipoteichoic acid and/or lactic acid bacteria producing it and/or its supernatant of culture, according to the invention, the nutritional formula may comprise a source of protein. Dietary proteins are preferably used as a source of protein. The dietary proteins may be any suitable dietary protein; for example animal proteins (such as milk proteins, meat proteins and egg proteins); vegetable proteins (such as soy protein, wheat protein, rice protein, and pea protein); mixtures of free amino acids; or combinations thereof. Milk proteins such as casein, whey proteins and soy proteins are particularly preferred. The composition may also contain a source of carbohydrates and a source of fat.

If the nutritional formula includes a fat source, the fat source preferably provides about 5% to about 55% of the energy of the nutritional formula; for example about 20% to about 50% of the energy. The lipids making up the fat source may be any suitable fat or fat mixtures. Vegetable fats are particularly suitable; for example soy oil, palm oil, coconut oil, safflower oil, sunflower oil, corn oil, canola oil, lecithins, and the like. Animal fats such as milk fats may also be added if desired.

A source of carbohydrate may be added to the nutritional formula. It preferably provides about 40% to about 80% of the energy of the nutritional composition. Any suitable carbohydrates may be used, for example sucrose, lactose, glucose, fructose, corn syrup solids, and maltodextrins, and mixtures thereof. Dietary fibre may also be added if desired. If used, it preferably comprises up to about 5% of the energy of the nutritional formula. The dietary fibre may be from any suitable origin, including for example soy, pea, oat, pectin, guar gum, gum arabic, and fructooligosaccharides.

Suitable vitamins and minerals may be included in the nutritional formula in an amount to meet the appropriate guidelines.

One or more food grade emulsifiers may be incorporated into the nutritional formula if desired; for example diacetyl tartaric acid esters of mono- and di-glycerides, lecithin and mono- and di-glycerides. Similarly suitable salts and stabilisers may be included.

The nutritional formula is preferably enterally administrable; for example in the form of a powder, tablet, capsule, a liquid concentrate, solid product or a ready-to-drink beverage. If it is desired to produce a powdered nutritional formula, the homogenised mixture is transferred to a suitable drying apparatus such as a spray drier or freeze drier and converted to powder.

In another embodiment, a usual food product may be enriched with at least one lipoteichoic from lactic acid bacteria according to the present invention. For example, a fermented milk, a yoghurt, a fresh cheese, a renneted milk, article of confectionery, for example a sweet or sweetened beverage, a confectionery bar, breakfast cereal flakes or bars, drinks, milk powders, soy-based products, non-milk fermented products or nutritional supplements for clinical nutrition.

In another embodiment a nutritionally complete pet food can be prepared. The nutritionally complete pet food may be in any suitable form; for example in dried form, semi-moist form or wet form; it may be a chilled or shelf stable pet food product. These pet foods may be produced as is conventional. Apart from the lipoteichoic acid according to the invention, these pet foods may include any one or more of a carbohydrate source, a protein source and lipid source.

Any suitable carbohydrate source may be used. Preferably the carbohydrate source is provided in the form of grains, flours and starches. For example, the carbohydrate source may be rice, barley, sorghum, millet, oat, corn meal or wheat flour. Simple sugars such as sucrose, glucose and corn syrups may also be used. The amount of carbohydrate provided by the carbohydrate source may be selected as desired. For example, the pet food may contain up to about 60% by weight of carbohydrate.

Suitable protein sources may be selected from any suitable animal or vegetable protein source; for example muscular or skeletal meat, meat and bone meal, poultry meal, fish meal, milk proteins, corn gluten, wheat gluten, soy flour, soy protein concentrates, soy protein isolates, egg proteins, whey, casein, gluten, and the like. The amount of protein provided by the protein source may be selected as desired. For example, the pet food may contain about 12% to about 70% by weight of protein on a dry basis.

The pet food may contain a fat source. Any suitable fat source may be used both animal fats and vegetable fats. Preferably the fat source is an animal fat source such as tallow. Vegetable oils such as corn oil, sunflower oil, safflower oil, rape seed oil, soy bean oil, olive oil and other oils rich in monounsaturated and polyunsaturated fatty acids, may also be used. In addition to essential fatty acids (linoleic and alpha-linoleic acid), the fat source may include long chain fatty acids. The amount of fat provided by the fat source may be selected as desired. For example, the pet food may contain about 5% to about 40% by weight of fat on a dry basis. Preferably, the pet food has a relatively reduced amount of fat.

The pet food may contain other active agents such as long chain fatty acids. Suitable long chain fatty acids include alpha-linoleic acid, gamma linoleic acid, linoleic acid, eicosapentanoic acid, and docosahexanoic acid. Fish oils are a suitable source of eicosapentanoic acids and docosahexanoic acid. Borage oil, blackcurrent seed oil and evening primrose oil are suitable sources of gamma linoleic acid. Safflower oils, sunflower oils, corn oils and soybean oils are suitable sources of linoleic acid.

The choice of the carbohydrate, protein and lipid sources is not critical and will be selected based upon nutritional needs of the animal, palatability considerations, and the type of product produced. Further, various other ingredients, for example, sugar, salt, spices, seasonings, vitamins, minerals, flavoring agents, gums, prebiotics and probiotic micro-organisms may also be incorporated into the pet food as desired.

Accordingly, the probiotic microorganism may be selected from one or more microorganisms suitable for animal consumption and which is able to improve the microbial balance in the intestine. The probiotic micro-organisms may be in powdered, dried form; especially in spore form for micro-organisms which form spores. Further, if desired, the probiotic micro-organism may be encapsulated to further increase the probability of survival; for example in a sugar matrix, fat matrix or polysaccharide matrix.

For dried pet foods a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food prior to processing. A suitable process is described in European patent application No 0850569. If a probiotic micro-organism is used, the organism is best coated onto or filled into the dried pet food. A suitable process is described in European patent application No 0862863.

For wet pet foods, the processes described in U.S. Pat. Nos. 4,781,939 and 5,132,137 may be used to produce simulated meat products. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers.

The following examples are given by way of illustration only and in no way should be construed as limiting the subject matter of the present application. Percentages and parts are by weight unless otherwise indicated. The examples are preceeded by a brief description of the figures.

FIG. 1. Effect of LTA from *L. johnsonii* strain La1 and *L. acidophilus* strain La10 on the release of IL-8 by HT29 cells challenged with LPS purified from *E. coli*. IL-8 production was measured by ELISA in supernatants of HT29 cells incubated for 24 hours in medium supplemented with 2% human milk (HM) in the presence of *E. Coli* LPS at 10 ng/ml (●) or 100 ng/ml (■) and varying amounts of LTA from La1 (A) or La10 (B). Activation of HT29 cells by LPS-HM alone is depicted as dashed lines. Error bars indicate SD. The results are representative of three independent experiments.

FIG. 2. Effect of LTA from lactobacilli La1 on the release of IL-8 by HT29 cells challenged with either LPS from *Sal. enteridis* or whole *E. coli* bacteria. IL-8 production was measured by ELISA in supernatants of HT29 cells incubated for 24 hours in medium supplemented with 2% human milk (HM) and either *Salmonella enteridis* LPS (A) at 10 ng/ml (●) or 100 ng/ml (■), or $2.5 \times 10^5$/ml whole *E. coli* bacteria (B) in the presence of varying amounts of LTA from La1. Activation of HT29 cells in the absence of LTA is depicted as dashed lines. Error bars indicate SD.

FIG. 3. Effect of LTA from the lactobacilli La1 and La10 on the release of TNF-α by HT29 cells challenged with *E. coli* LPS. TNF-α production was measured by ELISA in supernatants of HT29 cells incubated for 24 hours in medium supplemented with 2% human milk (HM) in the presence *E. Coli* LPS at 100 ng/ml and varying amounts of LTA from La1 (■) or La10 (●). Activation of HT29 cells in the absence of LTA is depicted as a dashed line. Error bars indicate SD.

Figure 4:
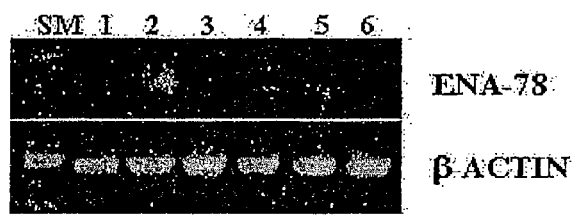
FIG. 4 shows the effect of LTA from the *lactobacillus* La1 on the LPS induction of ENA-78 mRNA expression in HT29 cells.

FIG. 4. Effect of LTA from the *lactobacillus* La1 on the LPS induction of ENA-78 mRNA expression in HT29 cells. ENA-78 expression was assessed by RT-PCR on total RNA of HT29 cells challenged with 100 ng/ml *E. Coli* LPS in the absence (lane 1) or the presence of 2% human milk (lanes 2 to 6), and the addition of MY4 anti-CD14 mAb (lane 3); isotype-matched antibody control (lane 4); or LTA from La1 at 1 μg/ml (lane 5) or 50 μg/ml (lane 6). The expected PCR product size for ENA-78 transcripts was 220 bp. For internal standard, amplified bands for β-actin (460 bp) were used as the house-keeping gene. SM, size marker.

Figure 5:
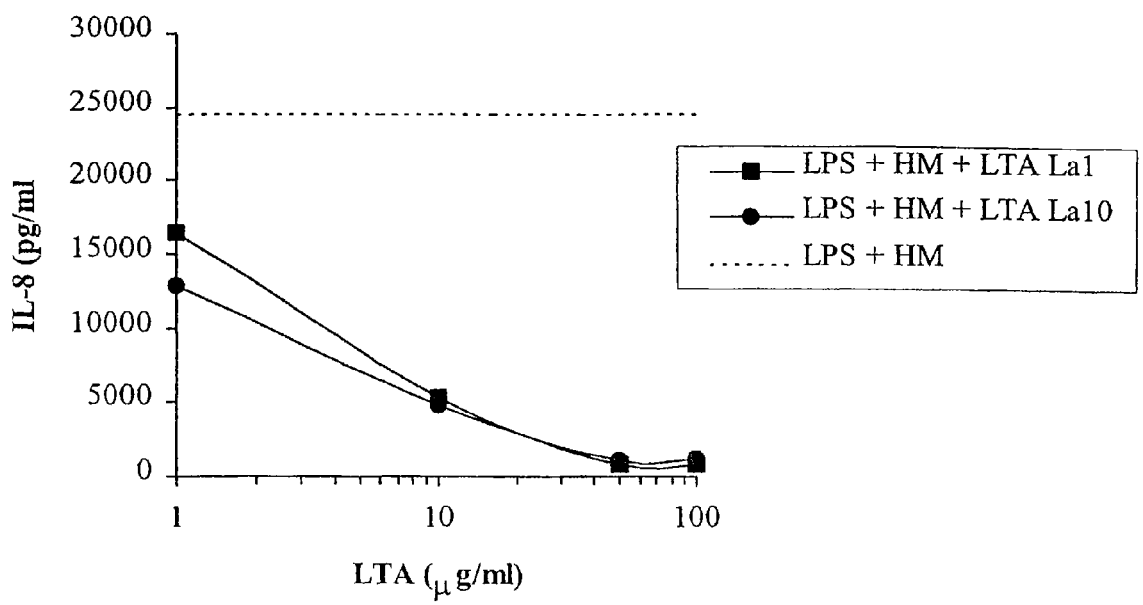
FIG. 5 shows the effect of LTA from the *lactobacilli* La1 and La10 on the release of IL-8 by differenciated HT29 cells challenged with *E. coli* LPS.

FIG. 5. Effect of LTA from the lactobacilli La1 and La10 on the release of IL-8 by differenciated HT29 cells challenged with *E. coli* LPS. IL-8 production was measured by ELISA in supernatants of differenciated HT29 cells incubated for 24 hours in medium supplemented with 2% human milk (HM) in the presence of *E. Coli* LPS 100 ng/ml and indicated amounts of LTA from *Lactobacillus* La1 (■) or La10 (●). Activation of differenciated HT29 cells in the absence of added LTA is depicted as dotted lines.

Figure 6:
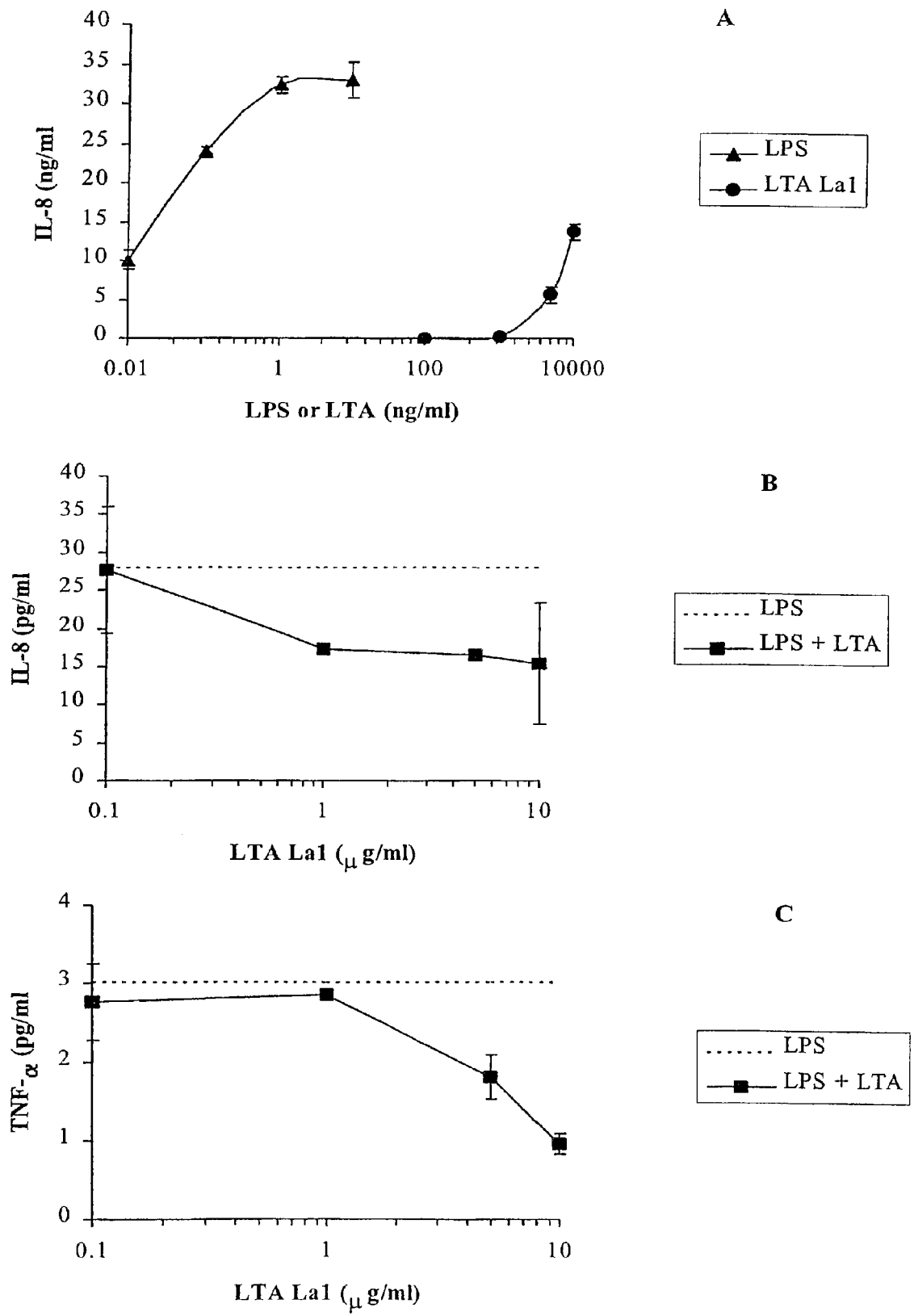
FIG. 6A shows the effect of LTA from the *lactobacillus* La1 on the activation of human PBMC and the presence of IL-8. Freshly isolated human PBMC ($2 \times 10^5$ cells/well) were incubated in RPMI supplemented with 1% human serum in the presence of varying amounts of either *E. coli* LPS or LTA from La1.
FIG. 6B shows the effect of LTA from the *lactobacillus* La1 on the activation of human PBMC and the presence of IL-8. PBMC were incubated for 30 min at 37° C. in the absence (dashed lines) or the presence (solid lines) of varying amounts of LTA from La1 before the addition of *E. Coli* LPS (1 ng/ml).
FIG. 6C shows the effect of LTA from the *lactobacillus* La1 on the activation of human PBMC and the presence of TNA-α. PBMC were incubated for 30 min at 37° C. in the absence (dashed lines) or the presence (solid lines) of varying amounts of LTA from La1 before the addition of *E. Coli* LPS (1 ng/ml).

FIG. 6. Effect of LTA from the *lactobacillus* La1 on the activation of human PBMC. (A) Freshly isolated human PBMC, ($2 \times 10^5$ cells/well) were incubated in RPMI supplemented with 1% human serum in the presence of varying amounts of either *E. coli* LPS ( ) or LTA from La1 (●). (B) and (C) PBMC were incubated for 30 min at 37° C. in the absence (dashed lines) or the presence (solid lines) of varying amounts of LTA from La1 before the addition of *E. Coli* LPS (1 ng/ml). After 24 hours incubation, the culture supernatants were collected and analysed for the presence of IL-8 (A) and (B), or TNF-α (C) by specific ELISA. Error bars indicate SD.

FIG. 7. Effect of deacylation of the LTAs on their antagonistic activity. HT29 cells were challenged with *E. coli* LPS (100 ng/ml) in medium supplemented with 2% human milk (HM) in the absence (dashed lines) or the presence (solid lines) of varying amounts of native LTA (■) or deacylated LTA (●) purified from either La1 (A) or La10 (B). After 24 hours, the release of IL-8 in the culture supernatants was measured by ELISA.

Figure 8:
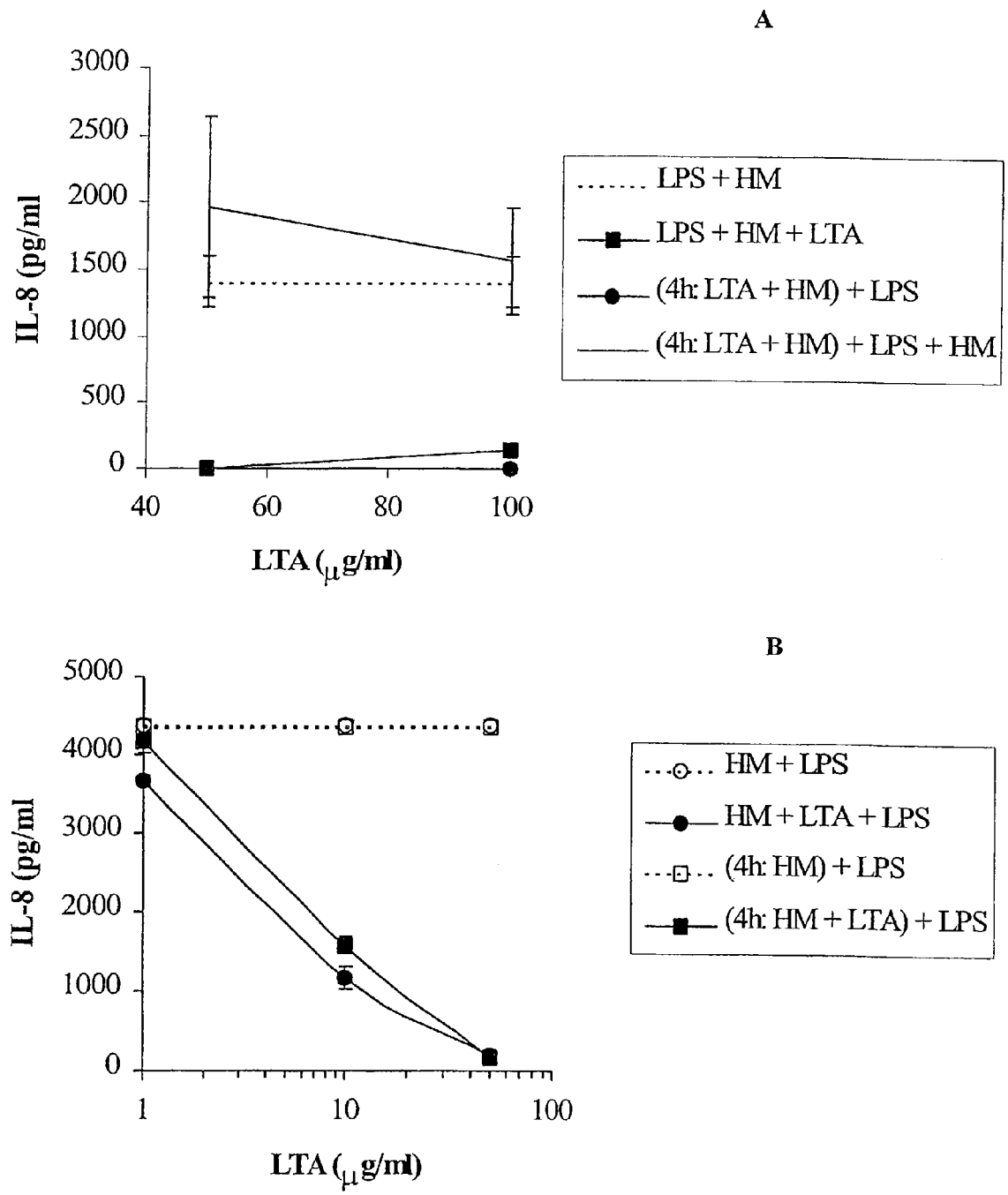
FIG. 8A shows the effect of pre-incubation of the cells with either LTA and sCD14 or LTA and LPS on the antagonism. HT29 cells were pre-incubated for 4 hours with La1 LTA (50 and 100 μ.g/ml) in the presence of 2% human milk (HM), washed twice with a serum-free media and then challenged for 20 hours with E. coli LPS (100 ng/ml) in the absence or the presence of HM. IL-8 release in the supernatants after a total of 24 hours culture was measured by ELISA.
FIG. 8B shows the effect of pre-incubation of the cells with either LTA and sCD14 or LTA and LPS on the antagonism. HT29 cells were incubated with La1 LTA (1, 10 and 50 μg/ml) in the presence of human milk (HM) for 4 hours before the addition of E. coli LPS (100 ng/ml). IL-8 release in the supernatants after a total of 24 hours culture was measured by ELISA.
FIG. 8C shows the effect of pre-incubation of the cells with either LTA and sCD14 or LTA and LPS on the antagonism. HT29 cells were incubated with La1 LTA (1, 10 and 50 μg/ml) in the presence of E. coli LPS (100 ng/ml) for 4 hours before the addition of 2% human milk (HM). IL-8 release in the supernatants after a total of 24 hours culture was measured by ELISA.
FIG. 8D shows the effect of pre-incubation of the cells with either LTA and sCD14 or LTA and LPS on the antagonism. HT29 cells were challenged with E. coli LPS (100 ng/ml) in the presence of 2% human milk (HM) for 4 hours before the addition of La1 LTA (1, 10 and 50 μg/ml). IL-8 release in the supernatants after a total of 24 hours culture was measured by ELISA.

FIG. 8. Effect of pre-incubation of the cells with either LTA and sCD14 or LTA and LPS on the antagonism. (A) HT29 cells were pre-incubated for 4 hours with La1 LTA (50 and 100 μg/ml) in the presence of 2% human milk (HM), washed twice with a serum-free media and then challenged for 20 hours with *E. coli* LPS (100 ng/ml) in the absence or the presence of HM. (B) HT29 cells were incubated with La1 LTA (1, 10 and 50 μg/ml) in the presence of human milk (HM) for 4 hours before the addition of *E. coli* LPS (100 ng/ml). (C) HT29 cells were incubated with La1 LTA (1, 10 and 50 μg/ml) in the presence of *E. coli* LPS (100 ng/ml) for 4 hours before the addition of 2% human milk (HM). (D) HT29 cells were challenged with *E. coli* LPS (100 ng/ml) in the presence of 2% human milk (HM) for 4 hours before the addition of La1 LTA (1, 10 and 50 μg/ml). IL-8 release in the supernatants after a total of 24 hours culture was measured by ELISA. Error bars indicate SD.

EXAMPLE 1

Lipoteichoic Acid from *Lactobacillus johnsonii* Strain NCC 533 and *Lactobacillus acidophilus* Strain NCC 90, Antagonise the Responsiveness of Human Intestinal Epithelial Cells to LPS or Gram-Negative Bacteria Materials and Methods
Cells, Media and Reagents.

The human colonic adenocarcinoma cell line HT29 was obtained from American Type Culture Collection (ATCC, Manassas, Va. ATCC: HTB-38). Undifferentiated cells were maintained in glucose-containing DMEM supplemented with 10% foetal calf sera (FCS; Amimed BioConcept, Allschwill, Switzerland) at 37° C. in a 5% $CO_2$/air incubator, while differentiated cells were grown in glucose-free medium. Culture medium was changed every 2 days until the cell monolayers reached 90% confluency. Human peripheral blood mononuclear cells (PBMC) were isolated from heparinised blood of healthy adult donors by Ficoll-Isopaque (Pharmacia) density gradient centrifugation. The isolated PBMC were washed three times and resuspended in RPMI 1640 medium (Life Technologies, address) supplemented with 1% FCS. LPS from *E. coli* and *Salmonella enteritidis* strains were purchased from Sigma Chemical Co. (St Louis, Mo.). Murine anti-CD14 monoclonal antibody MY4 (IgG2b) was purchased from Coulter (Instrumentation Laboratory AG, Switzerland).

The isotype-matched control mAb was mouse IgG2b (kappa), derived from MOPC 141 (Sigma). Human breast milk was obtained from healthy mothers. Samples were obtained up to 70 days postpartum by breast pump expression into sterile centrifugation tubes and processed within 2 hours of collection. After centrifugation at 200×g for 30 min, the acellular lipid-free fraction was frozen at −80° C. until used.
Isolation and Purification of LTAs.

LTAs of *Lactobacillus johnsoni* La1 NCC 533 and *Lactobacillus acidophilus* La 10 NCC 90 were isolated following the method of Fischer et al. (Fischer, W., et al. 1983. *Eur. J Biochem* 133:523-530). Briefly, bacteria were cultured overnight in MRS-broth, harvested and resuspended in 0.1 M sodium acetate pH 4.5 at 800 mg wet wt/ml of buffer. They were then defatted by mixing with two volumes of methanol and one volume of chloroform overnight at room temperature. The defatted bacteria were recovered by filtration, washed with two volumes of methanol and resuspended in 0.1 M sodium acetate pH 4.7 at a concentration of 500 mg of bacteria per ml of buffer. This suspension was mixed with an equal volume of hot 80% w/v aqueous phenol and stirred constantly for 45 minutes in a water bath at 65° C. After cooling, the emulsion which had formed, was centrifuged at 5000×g at 4° C. for 30 minutes. The upper aqueous layer was then extensively dialysed against 0.1 M sodium acetate pH 5

(cut off 6-8 kDa). Nucleic acids were digested with 30 U/ml DNAse I (Sigma), 9 U/ml ribonuclease A (Sigma) in 5 mM MgSO4, 40 mM EDTA disodium and 0.2 mM NaN3 (24 h at room temperature) with 1 ml of toluene added to prevent microbial contamination. The digest was dialysed once more against 0.1 M sodium acetate pH 4.7, and adjusted to 15% with 1-propanol. It was applied to an Octyl-sepharose column equilibrated in 0.1 M sodium acetate plus 15% 1-propanol, with a flow rate of 0.1 ml/minute. Fractions of 5 ml were collected. Elution of the LTA was done with a gradient of 15-80% 1-propanol in the same buffer, with a flow rate of 0.5 ml/minute. Fractions of 3 ml were collected. Monitoring of 1-propanol concentration was done by measuring the refraction index. Each fraction was analysed for its content of total neutral sugars (Dubois, M. A., et al. Colorimetric method for determination of sugars and related substances. *Anal Chem* 28:350-356), phosphorus (Chen, P. S., et al. 1956. Microdetermination of phosphorus. *Anal Chem* 28:1756-1758), nucleic acids and refraction index. The peaks were concentrated with a rotavap to get rid of the propanol, then extensively dialysed against water. After concentration, 0.1 M sodium acetate pH 4.7, 1 mM $CaCl_2$ and $MgCl_2$ was added and aliquots frozen at −20° C. The antigenic activity of La1 LTA was verified by ELISA as described recently (Granato, D., et al. 1999. *Appl Environ Microbiol* 65:1071-1077). Deacylation was done as described by Teti et al (Teti, G., et al. 1987. *Infect Immun* 55:3057-3064).

*Limulus* Amoebocyte Lysate Assay.

All reagents to which cells were exposed were tested for endotoxin contamination by a turbidimetric kinetic *Limulus* amebocyte lysate clot assay (E-Toxate® assay). The test had a sensitivity of 0.05-0.1 endotoxin units (*E. coli* 0.55:B5 LPS) per ml. The different media used in this study were found to be inactive or to contain <50 pg/ml of endotoxin.

Treatment of Cells.

HT29 cells were plated at $10^4$ cells/well in 96-well flat-bottom plates. After incubation for 5 days, HT29 cells were washed twice with serum-free media, before the addition of human milk, LPS and/or LTA in 200 µl of DMEM. In some wells, anti-CD14 monoclonal antibodies at a final concentration of 20 µg/ml were also added. In other experiments, PBMC were suspended in RPMI 1640 medium with 1% FCS and then plated at a concentration of $2 \times 10^5$ cells/well in 96-well flat-bottom plates. The cells were then incubated with LTA for 30 min at 37° C. and then stimulated with LPS. After 24 h incubation at 37° C., supernatants were collected and stored at −20° C. for future measurement of cytokine content. The cell viability was examined using a cytotoxicity detection kit (Roche Diagnostics), which measured the lactate dehydrogenase (LDH) activity released from the cytosol of damaged cells into the supernatant.

Concentrations of IL-8 and TNF-α in Culture Supernatants.

The amounts of IL-8 and generated in cell culture supernatants were measured by ELISA. Briefly, monoclonal antibodies against IL-8 (2 µg/ml. ImmunoKontakt, Bioggio, Switzerland) were coated onto 96-well plates (Nunc) by overnight incubation at 4° C. Plates were then washed twice with 0.05% Tween-20 in PBS. Non-specific binding was blocked by incubating the plates with 10% FCS in PBS for a further 2 h at room temperature. Samples or standard concentrations of recombinant cytokine (15.625 to 2000 pg/ml. ImmunoKontakt) in FCS-PBS were then added for 3 h at room temperature. Plates were then washed 4 times with PBS-Tween before addition of biotin-labeled anti-human IL-8 monoclonal antibody (1 µg/ml, ImmunoKontakt) for a further hour at room temperature. After 4 washes, streptavidin-peroxidase (0.5 µg/ml. KPL, Bioreba, Reinach, Switzerland) was added for 1 h at room temperature. Plates were then washed again, and the substrate (TMB peroxydase. KPL) added for 10-30 min. The enzymatic reaction was stopped by the addition of 1N HCl. Absorbance was read at 450 nm in an ELISA reader (Dynex Technologies). The detection limit was approximately 30 pg/ml. The amounts of TNF-α released into cell culture supernatants were measured by a commercially-available ELISA kit (R&D systems).

Reverse Transcription and Polymerase Chain Reaction (RT-PCR) Amplification of Epithelial Neutrophil Activator (ENA)-78.

Total cellular RNA was extracted from HT29 cells in tissue culture dishes using the Trizol method (GIBCO-BRL). RNA isolated from intestinal epithelial cells was reverse-transcribed with Moloney murine leukemia virus reverse transcriptase (Perkin-Elmer, address). Briefly, RNA samples (0.5 µg of total RNA), 0.5 unit of RNase inhibitor, 1 mM of each dNTP, 0.5 nmol/ml of specific 3' primer, 5 mM $MgCl_2$ and 1.25 units of reverse transcriptase were incubated in a total volume of 10 µl of reaction mixture containing the enzyme buffer supplied by the manufacturer.

The reaction mixture was incubated for 30 min at 42° C., and then heated for 5 min at 95° C. The reverse-transcribed products were then amplified with Gold DNA polymerase (Perkin Elmer) on a thermocycler (Biolabo, Scientific Instruments, Chatel St Denis, Switzerland). The PCR was performed in a total volume of 50 µl using 10 µl of the reverse-transcribed products in PCR buffer, 2 mM $MgCl_2$, 5 µM of each dNTP, 0.2 nmol/ml of both ENA-78-specific 3' antisense and 5' sense primers (CGTTCTCAGGGAGGCTC (SEQ. ID. NO. 1) and TCCTTCGAGCTCCTTGTG (SEQ. ID. NO. 2), respectively. Keates et al. 1997 Am. J. Physiol 273 G75-G82) and 1.25 units of DNA polymerase. After an initial denaturation of 10 min at 95° C., samples were amplified by 35 cycles of denaturation at 94° C. for 45 sec, annealing at 60° C. for 1 min, and extension at 72° C. of 1 min 30 sec, followed by a 7-min extension step at 72° C. All samples were subjected to RT-PCR for β-actin as a positive control. Samples of RT-PCR products were loaded onto a 1.2% agarose gels (containing ethidium bromide) in TAE buffer and separated by electrophoresis at 150 V for 1 hr. RT-PCR products were visualised under UV light. The correct size of the bands was determined by comparison with DNA size markers (Boehringer Mannheim).

Results

LTA from *Lactobacillus* Species Inhibit *E. coli*- or LPS-Induced IL-8, TNF-α and ENA-78 Releases by HT29 Cells.

We examined whether Gram-positive bacteria or their derivatives could also stimulate the human intestinal epithelial cells HT29 cells. Different Gram-positive organisms were incubated with HT29 cells in the presence or absence of human milk as a source of sCD14. In contrast to *E. coli*, the Gram-positive bacteria *L. sakei, L. casei, L. acidophilus* strain La10 and *L. johnhsonii* strain La1, as well as *Staphylococcus aureus* and *Staphylococcus epidermidis* were unable to stimulate the release of IL-8 by HT29 cells even in the presence of sCD14. Moreover, no IL-8 secretion was observed when LTA from La1, La10 or from *Staphylococcus aureus* were added at concentrations of up to 100 µg/ml.

Since sCD14 is known to recognise components of both Gram-negative and Gram-positive bacteria, we tested whether components of Gram-positive organisms, such as LTA, could antagonise the effect of Gram-negative bacteria on HT29 cells. To this end, HT29 cells were challenged with LPS (10 and 100 ng/ml) in the presence or absence of human milk as the source of sCD14, and various amounts of LTA from either La1 (FIG. 1A) or La10 (FIG. 1B). As expected, HT29 cells exposed to 10 or 100 ng/ml E. coli LPS in the presence of sCD14 released significant amounts of IL-8 (FIG. 1, dotted lines). The addition of LTA from either La1 (FIG. 1A, solid lines) or La10 (FIG. 1B, solid lines) caused a marked decrease in the LPS-induced IL-8 secretion. This inhibitory activity was dose-dependent with complete inhibition being observed using a 100 to 1000-fold excess of LTA. To confirm that the inhibitory activity of LTA was a general phenomenon, the antagonistic activity of LTA on the response of HT29 cells to another source of LPS was tested. As shown in FIG. 2A, LTA from La1 inhibited IL-8 secretion by HT29 cells challenged with 10 or 100 ng/ml of LPS from Salmonella enteridis. Moreover, LTA from La1 antagonised the effect of whole E. coli-sCD14 on HT29 cells (FIG. 2B).

As shown in FIG. 3, both LTA from La1 and from La10 also inhibited E. coli LPS-induced TNF-α release by HT29 cells. Furthermore, the LPS-induced expression of ENA-78 mRNA encoding was also markedly inhibited by LTA from La1 (FIG. 4). Of note, the observed inhibitory activities of Lactobacillus LTAs were not due to a cytotoxic effect of the LTA preparations on the HT29 cells, as no significant release of LDH could be detected in culture supernatants (data not shown).

LTA from La1 and La10 Inhibit the LPS-Induced IL-8 Release by Differentiated HT29 Cells.

As shown in FIG. 5, differentiated HT29 cells challenged with 10 ng/ml of E. coli LPS in the presence of human milk, released significant amounts of IL-8 (dotted line). As before, LTA from either La1 or La10 (solid lines) caused in a dose-dependent decrease of this secretion. Complete inhibition was observed at a 5000-fold excess of LTA.

LTA from La1 Inhibits LPS Stimulation of Human Monocytes.

A number of LTAs interact with membrane-bound CD14 on blood monocytes and macrophages, and stimulate the secretion of various cytokines. We therefore analysed the secretion of IL-8 and TNF-α by PBMC exposed to Lactobacillus LTAs. PBMC were incubated in the presence of increasing amounts of Lactobacillus LTA (100 to 10000 ng/ml) for 30 min before the addition of E. coli LPS at a concentration of 1 ng/ml. As shown in FIG. 6, when given alone, La1 LTA stimulated IL-8 secretion at concentrations of 5 µg/ml or higher (FIG. 6A), however, no stimulation of TNF-α release was seen at any of the concentrations tested. Furthermore, while LTA from La1 had only a weak antagonistic effect on the LPS-induced secretion of IL-8 by PBMC (FIG. 6B), it inhibited more significantly the LPS-induced TNF-α secretion in a dose dependent manner (FIG. 6C). LTA from La10, alone or with LPS, had no significant effect on IL-8 or TNF-α production.

The Biological Activity of Deacylated LTA.

Deacylation of LTA results in a loss of cellular biological activities. This implies that the lipid moiety of LTA is critical for immunomodulatory activity. We therefore examined the effect of deacylation of LTAs on their antagonism of LPS in our cellular models. As shown in FIG. 7, the antagonistic activity of LTA from La1 (FIG. 7A) and from La10 (FIG. 7B) toward the LPS-sCD14 induction of IL-8 by HT29 cells, was significantly weaker after deacylation. Thus, the antagonistic activity of Lactobacillus LTAs in our cellular system is also mediated by the lipid moiety.

Role of sCD14-LTA Interactions in the Inhibition of LPS-sCD14 Effects.

In order to understand how LTA may exert its antagonistic effect on Gram-negative bacteria, different treatment procedures in which HT29 cells were pre-incubated with LTA from La1 and either human milk sCD14 or E. coli LPS were performed. When HT29 cells were pre-incubated for 4 hours with La1 LTA (50 and 100 µg/ml) with or without human milk, washed twice with a serum-free media and then challenged for 20 hours with LPS (100 ng/ml) in the presence of milk, the secretion of IL-8 was not abrogated (FIG. 8A). However, when the cells were pre-incubated for 4 hours with La1 LTA (1 to 50 µg/ml) in the presence of sCD14, and then, without washing, challenged for 24 hours with LPS (100 ng/ml), the level of IL-8 production was similar to that obtained when HT29 cells were incubated for 24 hours with LTA, LPS and sCD14 together (FIG. 8B). FIG. 8C shows the level of IL-8 production obtained 24 hours after the addition of the source of sCD14 to cells preincubated for 4 hours with La1 LTA (1-50 µg/ml) and LPS (100 ng/ml). This level was similar to the amount obtained when HT29 cells were incubated for 24 hours with the mixture LTA, LPS and sCD14. Similar results were obtained when the cells were preincubated for 4 hours with LPS (100 ng/ml) and the source of CD14 before addition of LTA (FIG. 8D).

IEC do not express membrane CD14 and require the soluble form to respond to LPS in vitro (Pugin, J., et al. 1993 PNAS 90:2744-2748). We have previously shown that Gram-negative bacteria and LPS mediate pro-inflammatory cytokine production in IECs through the action of a human milk sCD14 (Labeta, M. O., et al. 2000. J Exp Med 191:1807-1812). However, the IECs are unresponsive to various sources of LTA, in spite of the presence of sCD14. Since other studies suggest that binding of LTA to eukaryotic cell membranes requires fatty acid moieties and since fatty acid binding proteins are only expressed on differentiated IECs in the upper portion of the intestinal villus, we also examined LTA-milk effects on differentiated HT29. Interestingly, LTAs still failed to elicit any response, whereas LTAs from L. johnsonii strain La1 and L. acidophilus strain la10 were able to stimulate IL-8 release from blood monocytes.

These results lend further support to the probiotic status of the L. johnsonii strain La1 and L. acidophilus strain La10 and suggest a therapeutic role for their LTA in combatting diseases caused by Gram-negative bacteria or their derivatives.

EXAMPLE 2

Infant Formula

To obtain an infant formula we prepare the following mixture containing for 100 ml of formula: 0.5 to 5%, preferably 2% of peptides, 0.2 to 10%, preferably 4% of fat, 1 to 25%, preferably 8% of non-levan carbohydrates (including lactose 65%, maltodextrin 20%, starch 15%), and at least 106 cfu/ml of the following strains: Lactobacillus acidophilus NCC 90 (CNCM I-2332) or Lactobacillus johnsonii NCC 533 (CNCM I-1225), in combination with traces of vitamins and oligoelements to meet daily requirements, and 0.01 to 2%, preferably 0.3%, of minerals, and 50 to 90%, preferably 75% of water.

EXAMPLE 3

Use in Dairy Products

One or more strain of Lactobacillus acidophilus NCC 90 (CNCM I-2332) or Lactobacillus johnsonii NCC 533 (CNCM 1-1225), according to the present invention may be used for the manufacture of fermented yoghurt-like milk products.

To do this, 1 l of a milk product containing 2.8% of fats and supplemented with 2% of skimmed milk powder and 6% of sucrose is prepared, it is pasteurised at 96° C. for 30 minutes and its temperature is then lowered to 42° C. Precultures of a non-thickening strain of *Streptococcus thermophilus* and of a non-viscous strain *Lactobacillus bulgaricus* are reactivated in a sterile MSK culture medium containing 10% of reconstituted milk powder and 0.1% of commercial yeast extract.

A preculture of one or more of the strain is also reactivated in a medium containing 10% of reconstituted milk powder and 0.1% of commercial yeast extract with 1% sucrose. The pasteurised milk product is then inoculated with 1% of each of these reactivated precultures and this milk product is then allowed to ferment at 32° C. until the pH reaches a value of 4.5. Fermented milks yoghurt-like products are produced in this way and stored at 4° C.

EXAMPLE 4

Dry Pet Food

A feed mixture is made up of about 58% by weight of corn, about 6% by weight of corn gluten, about 23% by weight of chicken meal, salts, vitamins and minerals making up the remainder.

The feed mixture is fed into a preconditioner and moistened. The moistened feed is then fed into an extruder-cooker and gelatinised. The gelatinised matrix leaving the extruder is forced through a die and extruded. The extrudate is cut into pieces suitable for feeding to cats, dried at about 110° C. for about 20 minutes, and cooled to form pellets. At this point, a lyophilized powder of one or more strains of the following *Lactobacillus* species is provided for application to the pellets: *Lactobacillus johnsonii* NCC533 (CNCM I-1225) or *Lactobacillus acidophilus* NCC 90 (CNCM I-2332). Sufficient powder is thus provided so that the corresponding dietary intake amount for the pet is from about 1.0E+07-1.0E+9 cfu/day. Some of the powder is mixed into a first mass of pellets and bagged. A second quantity of the powder is measured out and mixed with a lipid carrier which is then sprayed on to a second mass of pellets. The pellets are bagged after the coating has dried sufficiently at 50-60° C. for some minutes.

This dry dog food is particularly intended for decreasing inflammatory process associated with bacterial colonization.

The invention claimed is:

1. A method for reducing inflammatory processes associated with bacteria in a human or an animal, the method comprising:
    orally administering to the human or animal a composition comprising a therapeutically-effective amount of a lipoteichoic acid from a lactic acid bacteria in combination with sCD 14 as an active ingredient, wherein the composition is in a form selected from the group consisting of a powder, a tablet, a capsule, a liquid concentrate, a solid product, a ready-to-drink beverage, a pet food, a pharmaceutical composition, a food composition and combinations thereof.

2. The method of claim 1, wherein the composition comprises at least one of a protein, a carbohydrate and a fat.

3. The method of claim 2, wherein the protein is selected from the group consisting of animal protein, vegetable protein, milk protein, free amino acids and combinations thereof.

4. The method of claim 2, wherein the fat is selected from the group consisting of animal fat, vegetable fat, milk fat and combinations thereof.

5. The method of claim 2, wherein the carbohydrate is selected from the group consisting of sucrose, lactose, glucose, fructose, corn syrup solids, maltodextrins and combinations thereof.

6. The method of claim 1, wherein the lactic acid bacteria belongs to a genus selected from the group consisting of *Lactobacillus, Bifidobacterium* and *Streptococcus*.

7. A method of modulating an immune response induced by Gram negative bacteria, potential pathogenic Gram positive bacteria, or their derivatives in a human or an animal, the method comprising:
    orally administering to the human or animal, a therapeutically-effective amount of composition comprising as an active ingredient sCD14 in combination with a component selected from the group consisting of a lipoteichoic acid from a lactic acid bacteria, a lactic acid bacteria producing lipoteichoic acid, a culture supernatant of a lactic acid bacteria producing lipoteichoic acid and combinations thereof.

8. The method of claim 7, wherein the composition comprises at least one of a protein, a carbohydrate and a fat.

9. The method of claim 8, wherein the protein is selected from the group consisting of animal protein, vegetable protein, milk protein, free amino acids and combinations thereof.

10. The method of claim 8, wherein the fat is selected from the group consisting of animal fat, vegetable fat, milk fat and combinations thereof.

11. The method of claim 8, wherein the carbohydrate is selected from the group consisting of sucrose, lactose, glucose, fructose, corn syrup solids, maltodextrins and combinations thereof.

12. The method of claim 7, wherein the composition is in a form selected from powder, tablet, capsule, a liquid concentrate, solid product, a ready-to-drink beverage, a pet food, a pharmaceutical composition, a food composition and combinations thereof.

13. The method of claim 7, wherein the lactic acid bacteria belongs to a genus selected from the group consisting of *Lactobacillus, Bifidobacterium* and *Streptococcus*.

14. A method of modulating an immune response induced in a pet animal by Gram negative bacteria, potential pathogenic Gram positive bacteria or their derivatives, the method comprising:
orally administering to the pet animal a pet food composition containing a moiety of a probiotic bacterial strain capable of modulating the immune response in combination with sCD14.

15. The method of claim 14, wherein the probiotic bacterial strain is capable of at least transiently adhering to the intestinal epithelium of the pet animal.

16. The method of claim 14, wherein the probiotic bacterial strain is a lactic acid bacteria having lipoteichoic acid.

17. The method of claim 14, wherein lactic acid bacteria belongs to a genus selected from the group consisting of *Lactobacillus, Bifidobacterium* and *Streptococcus*.

18. The method of claim 14, wherein the composition comprises at least one of a protein, a carbohydrate and a fat.

19. The method of claim 18, wherein the protein is selected from the group consisting of muscular meat, skeletal meat, meat meal, bone meal, poultry meal, fish meal, milk proteins, corn gluten, wheat gluten, soy flour, soy protein concentrates, soy protein isolates, egg proteins, whey, casein, gluten and combinations thereof.

20. The method of claim 18, wherein the fat is selected from the group consisting of animal fat, vegetable fat, milk fat and combinations thereof.

21. The method of claim 18, wherein the carbohydrate is selected from the group consisting of grains, flours, starches and combinations thereof.

22. The method of claim 14, wherein the pet food composition comprises a long chain fatty acid.

23. The method of claim 14, wherein the pet food composition comprises a wet pet food formulation.

24. The method of claim 14, wherein the pet food composition comprises a dry pet food formulation.

* * * * *